United States Patent [19]

Hodakowski et al.

[11] Patent Number: 5,139,152

[45] Date of Patent: Aug. 18, 1992

[54] WATER DISPERSIBLE GEL FORMULATIONS

[75] Inventors: Leonard E. Hodakowski; Chi-yu R. Chen; Samuel T. Gouge, all of Raleigh; Paul J. Weber, Durham, all of N.C.

[73] Assignee: Rhone-Poulenc AG Company, Research Triangle Park, N.C.

[21] Appl. No.: 713,701

[22] Filed: Jun. 11, 1991

Related U.S. Application Data

[63] Continuation-in-part of Ser. No. 680,308, Apr. 4, 1991, abandoned, which is a continuation-in-part of Ser. No. 679,290, Apr. 2, 1991, and a continuation-in-part of Ser. No. 554,615, Jul. 18, 1990, Pat. No. 5,080,226.

[51] Int. Cl.$^5$ ..................... A01N 25/04; B65D 85/82
[52] U.S. Cl. .......................... 206/524.7; 71/DIG. 1; 424/409; 424/412
[58] Field of Search ............... 71/DIG. 1; 206/0.5, 206/205, 219, 521, 524.1, 524.6, 524.7; 220/88.3; 383/113; 424/409, 412; 514/801, 944

[56] References Cited

U.S. PATENT DOCUMENTS

| | | | |
|---|---|---|---|
| 2,870,058 | 1/1959 | Loder | 167/42 |
| 3,117,606 | 1/1964 | Hastings | 206/521 |
| 3,123,117 | 3/1964 | Nourse et al. | 206/521 |
| 3,145,747 | 8/1964 | Nourse et al. | 206/521 |
| 3,171,779 | 3/1965 | McCoy et al. | 167/42 |
| 3,630,896 | 12/1971 | Oka et al. | 252/1 |
| 3,661,695 | 5/1972 | Berliner | 161/151 |
| 3,695,989 | 10/1972 | Albert | 161/160 |
| 3,892,905 | 7/1975 | Albert | 428/220 |
| 4,244,728 | 1/1981 | Dellicolli et al. | 71/DIG. 1 |
| 4,341,078 | 7/1982 | Weitzen | 220/88.3 |
| 4,416,791 | 11/1983 | Haq | 252/90 |
| 4,626,372 | 12/1986 | Kaufman et al. | 252/90 |
| 4,657,582 | 4/1987 | Huber | 71/DIG. 1 |
| 4,681,228 | 7/1987 | Kerry et al. | 206/484 |
| 4,767,441 | 8/1988 | Walker et al. | 71/DIG. 1 |
| 4,846,992 | 7/1989 | Fonsny | 252/90 |
| 4,849,141 | 7/1989 | Fujioka et al. | 514/801 |
| 4,885,105 | 12/1989 | Yang et al. | 252/90 |
| 4,933,447 | 6/1990 | Philips et al. | 71/DIG. 1 |
| 4,969,750 | 11/1990 | Russo et al. | 383/113 |
| 4,975,113 | 12/1990 | Marrs et al. | 71/DIG. 1 |
| 4,985,062 | 1/1991 | Hughes | 71/DIG. 1 |
| 5,045,109 | 9/1991 | Nakamura et al. | 71/DIG. 1 |

FOREIGN PATENT DOCUMENTS

| | | |
|---|---|---|
| 0132726 | 2/1985 | European Pat. Off. . |
| 0234867 | 9/1987 | European Pat. Off. . |
| 0251464 | 1/1988 | European Pat. Off. . |
| 317260 | 5/1989 | European Pat. Off. . |
| 420497 | 4/1991 | European Pat. Off. . |
| 3017246 | 11/1981 | Fed. Rep. of Germany . |
| 47-1800 | 1/1972 | Japan . |
| 53-26868 | 3/1978 | Japan . |
| 55-4336 | 1/1980 | Japan . |
| 62-192301 | 8/1987 | Japan . |
| 2-108534 | 4/1990 | Japan . |
| 8912587 | 12/1989 | PCT Int'l Appl. . |
| 8912588 | 12/1989 | PCT Int'l Appl. . |
| 8912589 | 12/1989 | PCT Int'l Appl. . |
| 8912590 | 12/1989 | PCT Int'l Appl. . |
| 9105714 | 5/1991 | PCT Int'l Appl. . |
| 0013504 | of 1912 | United Kingdom . |
| 0922317 | 3/1963 | United Kingdom . |

OTHER PUBLICATIONS

L. M. Rogiers, ICI Specialty Chemicals, *New Formulation Trends in the Agricultural Industry*, Reprint #RP25/88E, pp. 3–11 (Nov. 1988).

B.F. Goodrich, Carbopol ® Water Soluble Resins, p. 5 (Sep. 1987).

*Research Disclosure*, No. 28928, New York, N.Y. (May 1988).

Derwent Abstract 87-274684 of Japanese Patent Application 62-192301 (1987).

Abstract of Japanese Patent Application 53-76890 (Patent No. 55-4336) (1980).

Derwent Abstract 72-04999T of Japanese Patent Application 47-1800 (1972).

Derwent Abstract 88-194649 of Japanese Patent Application 63-132802 (1988).

Abstract of Japanese Patent Application 54-143131 (Patent No. 56-68601) (1981).

*Primary Examiner*—Jimmy G. Foster
*Attorney, Agent, or Firm*—Morgan & Finnegan

[57] ABSTRACT

A gel formulation comprising a hazardous material, such as a hazardous chemical, and sufficient surfactant such that it meets certain test requirements. A containerization system for same.

49 Claims, No Drawings

WATER DISPERSIBLE GEL FORMULATIONS

This application is a continuation-in-part of U.S.. Pat. application No. 07/680,308, now abandoned, filed Apr. 4, 1991, which is a continuation-in-part of U.S. Pat. application No. 07/679,290, filed Apr. 2, 1991, and U.S. Pat. application No. 07/554,615 filed July 18, 1990, Pat. No. 5,080,226, al of which are incorporated herein by reference.

BACKGROUND OF THE INVENTION

I. Field of the Invention

The invention relates to new compositions comprising hazardous products and which are nevertheless safe for the handling and the environment.

II. Discussion of Background

At present, most hazardous liquids are stored in metal drums or, where smaller quantities are required, plastic containers.

Hazardous compounds, especially agrochemical compounds, are formulated in various compositions. Liquid compositions are most convenient for farmers because of the relative ease with which they can be handled. There are, nevertheless, difficulties in handling such liquid compositions. There is a danger of spillage or leakage if there are holes in the containers previously used or if they are dropped. Secure containers, resistant to shock, can be used. However, in the event of an accident, for example during transportation, the risk remains of spillage or leakage with rapid loss of liquid, for example leaking onto the ground.

It has been difficult to provide a formulation and containing system which safeguards those handling it, including farmers and transporters, and the environment.

SUMMARY OF THE INVENTION

An object of the present invention is to provide a new formulation system to contain agrochemicals which is safe for everybody, and the environment.

Another object of the present invention is to provide a new formulation system for agrochemicals which is easy to put in a containing system and which is easy to manipulate for the farmer.

Another object of the present invention is to provide a new formulation system for agrochemicals which is readily, rapidly and easily soluble and/or dispersible in water.

Another object of the present invention is to provide a new formulation system for agrochemicals which is as much condensed as possible, using the least amount of space.

Another object of the present invention is to provide a new formulation system to contain hazardous compounds, e.g., agrochemicals which diminish the risks of pollution.

It is also known that liquid agrochemicals may be contained in soluble bags or sachets made from films. However, such films may crack and break. This causes spillage of the agrochemicals they contain and creates contamination problems. In fact, there are a variety of defects which may be present in films, which lead to weaknesses of film and consequently a potential source of leakage. The presence of air bubbles, or dust particles or foreign bodies, or gel particles or thin points on or in the film are all potential weak points. If a film with such a weak point is subjected to a lot of handling or physical shocks, the film may fail at that point. This is especially a problem in the agrochemical industry where containers may be subjected to rough or unsafe handling by distributors or farmers.

Another object of the present invention is to avoid leakage through pinholes when an agrochemical containing bag is used. Such pinholes are rare, but only one pinhole among thousands of bags is enough to cause a lot of trouble, because the liquid going through the pinhole contaminates all of its environment.

Another object of the present invention is to avoid breakage of the container which contains an agrochemical formulation. When the container is rigid, there is substantial possibility of simple breakage. With a liquid in a bag this possibility is somewhat reduced, but the liquid still transmits the shocks and there is the problem of hydraulic hammer effect. An object of the instant invention is to avoid, or at least to partially reduce, this hydraulic hammer effect. It has been proposed to reduce the possibility of breakage by means of an air space in the bag, but this represents some loss of storage space.

Another object of the present invention is to have a formulation or composition for hazardous compounds which dissipate, as much as possible, the energy of a shock to a container from outside.

Another object of the present invention is to provide a shock absorbing formulation system for containing agrochemcials, e.g., pesticides or plant protection agents or plant growth regulators.

It was known to use gel formulations for pharmaceutical or cosmetics, but there is practically no risk of pollution or contamination of the environment when handling such products, in contrast to pesticides and agrochemicals. Furthermore, the gels used for pharmaceutical or cosmetic purposes are generally water-based. Thus, it was unobvious to obtain gels which are convenient for water soluble sachets or bags, for pesticide containing water soluble sachets or bags, or for shock absorption purposes for such bags.

Another possibility is to have agrochemicals in the form of wettable powders in a bag which may be water soluble. However, not all agrochemcials may be used under the form of a wettable powder. Even if these powders are wettable, the length of time to get the powder wetted (wetting time) may cause some technical problems.

As already said, other containing systems for pesticides which are safe for the environment have been proposed in the past, especially those containing liquid in soluble bags or sachets. However it may happen that the bags have pinholes; the contained liquid leaks in such conditions and may pollute the environment.

Even though thixotropic liquid may be used, this possibility of leakage through pinholes remains when shipping, because the shipping creates a movement which causes the thixotropic liquid becomes more fluid.

Furthermore even the non aqueous liquid contained in the known water soluble bags may have a low, but non zero, content of water, and this content, even though it is low, may cause the bags breaking upon freezing.

The present invention seeks to provide a new formulation system for agrochemicals which quickly dissolves when put into water and which is not damaged by normal freezing.

A further object of the present invention is to provide a formulation system wherein less solvent is needed in the formulation of the pesticide, which is cost saving both in shipping and manufacturing.

The invention further seeks to provide a new formulation system for agrochemicals which reduces the risks of clogging the spray nozzles or the filters of spray tanks.

Other objects and advantages of the invention will better appear from the following description. The objects of the invention can be achieved in full or in part by means of the invention.

The present invention relates to a water dispersible organic gel comprising a hazardous product and sufficient water soluble surfactant to meet the following test: the hazardous product (50 g) and the surface-active adjuvant (5 g) are added to an amount of water, at 50° C., which is sufficient to bring the volume of the mixture to 100 ml; the mixture is agitated so as to give a homogenous emulsion and this is left to stand for 30 minutes at 50° C. in a graduated cylinder; the amount of oily layer which may have separated out (and thus formed a distinct liquid phase) must then be less than 20 ml. It also includes a gelling agent which can be either liquid or solid at 23° C. and which is soluble at less than 10% in the liquid mixture of active ingredient and surfactant above 50° C., this gelling agent having, when it is a solid, a particles size lower than 100 microns, preferably less than 20 microns; and less than 3% by weight of water, preferably less than 1%.

DESCRIPTION OF THE PREFERRED EMBODIMENT

The present invention provides formulations or compositions which are especially suitable to be contained in a water soluble or water dispersible bag containing a water dispersible organic gel which is a continuous system comprising effective amounts of:

a hazardous product;

a water soluble or water dispersible surfactant, which may be non ionic or anionic or cationic or may have more than one of these characteristics. This surfactant(s) will satisfy the following test: the hazardous product (50 g) and the surface-active adjuvant (5 g) are added to an amount of water, at 50° C., which is sufficient to bring the volume of the mixture to 100 ml; the mixture is agitated so as to give a homogenous emulsion and this is left to stand for 30 minutes at 50° C. in a graduated cylinder; the amount of oily layer which separates out (and thus forms a distinct liquid phase) must then be less than 20 ml;

a gelling agent which is either liquid or solid at 23° C. and which is soluble at less than 10% in the liquid mixture of active ingredient and surfactant above 50° C., this gelling agent having, when it is solid, a particles size lower than 100% microns, preferably less than 20 microns; and less than 3% by weight of water, preferably less than 1%.

The hereinbefore defined gel may optionally contain the further following components:

an organic solvent (this word includes a mixture of individual solvents) wherein the active ingredient is completely soluble at the given concentration;

a dispersant;

a secondary thickener; and/or other additives, such as stabilizer(s), antifoaming agent(s), buffer(s), antifreezing agent(s).

Among the gels of the invention as hereabove defined, some particular gels are preferred, especially those comprising:

5 to 95%, more preferably 25 to 80%, of the active ingredient;

1 to 50%, more preferably 2 to 15%, of the surfactant;

0.1 to 50%, more preferably 2 to 10%, of the gelling agent(s);

0.1 to 30%, more preferably 1 to 25%, of the secondary thickener;

0 to 80% of the solvent, more preferably 3 to 50%; and 0 to 20% of other additives (as hereinbefore defined), preferably 0.1 to 10%.

When gels of the invention contain a dispersant, they preferably comprise 1 to 25%, more preferably 2 to 8%, of the dispersant.

Preferred gels of the invention are also those which contain a surfactant which is able to form above 70° C., preferably above 50° C., a liquid phase with the active ingredient (or hazardous product).

According to a particular feature of the invention, the components of the compositions are chosen in such a way that the gels of the invention have a viscosity of 600 to 30,000 centipoises, more preferably of 1000 to 12000 centipoises. These viscosities are Brookfield viscosities measured with a viscosimeter in the form of a flat plate rotating at 20 revolutions per minute.

By the term "continuous system", it is meant a material which is visually homogeneous, that is to say which has the visual appearance to have only one physical phase. This does not exclude the possibility to have small solid particles dispersed therein, provided these particles are small enough not to constitute a visible separate physical phase.

It is known that a gel is generally a colloid in which the dispersed phase has combined with the continuous phase to produce a viscous jelly-like product; it is also a dispersed system consisting typically of a high molecular weight compound or aggregate of small particles in very close association with a liquid. In the gels of the invention, the hazardous product (or active ingredient) may be in a soluble form, or in a dispersed form such as in a suspension.

According to one feature, the gels of the invention preferably have a density greater than 1, preferably greater than 1.05.

According to a particular feature of the invention, the components of the compositions are chosen in such a way that the gels of the invention have a spontaneity (as hereafter defined) less than 75, preferably less than 25.

The spontaneity is assessed according to the following method: A mixture of 1 ml gel with 99ml water are put into a 150ml glass tube which is stoppered and inverted through 180° (upside down). The number of times required to completely disperse the gel is called the spontaneity.

By the word surfactant, it is meant an organic material which is able to substantially reduce the surface tension of water which is 73 dynes/cm at 20° C.

The surfactant which may be used in the invention may be selected from among those of the following list (which is non limiting; provided that the physical requirements of the surfactant are met):

alkanolamides, poly condensates of ethylene oxide with fatty alcohols, fatty esters, or fatty amines, or substituted phenols (particularly alkylphenols or arylphenols); block copolymers with ethoxy and propoxy groups; esters of fatty acids with polyols such as glycerol or glycol; polysaccharides; organopolysiloxanes; sorbitan derivatives; ethers or esters of sucrose or glucose; salts of lignosulphonic acids, salts of phenyl sulphonic or naphthalene sulphonic acids, diphenyl sulfonates; alkyaryl sulfonates; sulfonated fatty alcohols or amines or amides; poly condensates of ethylene oxide with fatty acids and their sulfate or sulfonate derivatives; salts of sulphosuccinic or sulfosuccinamic acid esters; taurine derivatives (particularly alkyltaurates); betaine derivatives; phosphoric esters of alcohols or of polycondensates of ethylene oxide with phenols; and sulphate, sulphonate and phosphate functional derivatives of the above compounds.

By the wording "gelling agent", it is meant a material corresponding to the active ingredient in such a way that, when mixed, at 50/50 w/w and 25° C., with (and optionally grinded with) an organic solvent wherein the active ingredient is soluble, a gel is obtainable. According to the present invention, a gel is essentially a material which has a phase different phi between the controlled shear stress and the resulting shear strain such that tg(phi) is less than or equal to 1.5, preferably less than or equal to 1.2. Tg(phi) is the tangent of the angle phi (or phase difference). The measurement of phi is made by means of a rheometer having a flat fixed plate and a rotating cone above this plate such as the angle between them is less than 10°, preferably 4°. The cone is caused to rotate by means of a controlled speed motor; the rotation is a sinusoidal one, i.e., the torque and the angular displacement change as a sine function time. This angular displacement corresponds to the hereabove mentioned shear strain; the torque of the controlled speed motor (which causes the angular displacement) corresponds to the hereabove mentioned controlled shear stress.

Gelling agent which may be used in the invention are tetramethyl decyne diol, ethoxylated diakylphenol, methylated clay, propylene carbonate, hydrogenated castor oil, ethoxylated vegetable oil, diatomaceous earth, mixture of dioctyl sodium sulfosuccinate and sodium benzoate, mixtures of hexanediol and hexanediol.

By the expression "hazardous product" as used herein is meant a product (material) which may cause damage to the environment or be injurious to a person handling it.

According to one main and preferred feature of the invention, the hazardous product is an active ingredient which is an agrochemical, and more precisely a pesticide or a plant protection agent (including plant growth regulators or plant nutrients).

The invention is not limited to some specific agrochemicals; a list of many agrochemicals which can be used in the invention includes:

Fungicides such as Triadimefon, Tebuconazole, Prochlaraz, Triforine, Tridemorph, Propiconazole, Pirimicarb, Iprodioine, Metalaxyl, Bitertanol, Iprobenfos, Flusilazol, Fosetyl, Propyzamide, Chlorothalonil, Dichlone, Mancozeb, Anthraquinone, Maneb, Vinclozolin, Fenarimol, Bendiocarb, Captafol, Benalaxyl, Thiram;

Herbicides (or defoliants) such as quizalofop and its derivatives, Acetochlor, Metolachlor, Imazapur and Imazapyr, Glyposate and Gluphosinate, Butachlor, Aciflourfen, Oxyfluorfen, Butralin, Fluazifop-butyl, Bifenox, Bromoxynil, Ioxynil, Diflufenican, Phenmedipham, Desmedipham, Oxadiazon, Mecopropo, MCPA, MCPB, MCPP, Linuron, Isoproturon, Flamprop and its derivatives, Ethofumesate, Diallate, Carbetamide, Alachlor, Metsulfuron, Chlorsulfuron, Chlorpyralid, 2,4-d, Tribufos, Triclopyr, Diclofop-methyl, Sethoxydim, Pendimethalin, Trifluralin, Ametryn, Chloramben, Amitrole, Asulam, Dicamba, Bentazone, Atrazine, Cyanazine, Thiobencarb, Prometryn, 2-(2-chlorobenzyl)-4, 4-dimethyl-1,2-oxazolidin-3-one, Fluometuron, Napropamide, Paraquat, Bentazole, Molinate, Propachlor, Q Imizaquin, Metribuzin, Tebuthiuron, Oryzalin; and Insecticides or nematicides such as Ebufos, Carbosulfan, Amitraz, Vamidothion, Ethion, Triazophos, Propoxur, Phosalone, Permethrin, Cypermethrin, Parathion, Methylparathion, Diazinon, Metomyl, Malathion, Lindane, Fenvalerate, Ethoprophos, Endrin, Endosulfan, Dimethoate, Dieldrin, Dicrotophos, Dichloroprop, Dichlorvos, Azinpohs and its derivatives, Aldrin, Cyfluthrin, Deltamethrin, Disulfoton, Chlordimeform, Chlropyrifos, Carbaryl, Dicofol, Thiodicarb, Propargite, Demeton, Phosalone.

Plant growth regulators such as gibberellic acid, ethrel or ethephon, cycoccl, Chlormequat, Ethephon, Mephiquat.

In order to assess whether a surface-active adjuvant possesses dispersing properties and may be a dispersant according to the invention, the following test is carried out: an aqueous suspension (100 ml) containing kaolin or atrazine (50 g), in the form of solid particles having a particle size between 1 and 10 microns, and the surface-active adjuvant (5 g) is left to stand at 20° C. for 30 minutes in a graduated cylinder (kaolin is used when the dispersing agent is able to disperse a hydrophilic solid. Atrazine is used when the dispersing agent is able to disperse a hydrophobic solid). After standing, 9/10ths (nine-tenths) of the volume of the suspension, situated in the upper part of the suspension, is removed, without agitation, and the solids content (residue after evaporation of the water) of the remaining tenth is measured; this solids content must not exceed 12% by weight of the solids content of 100 ml of the suspension on which the test is carried out.

The dispersant which may be used in the invention may be selected among those of the following list (which is non limiting): salts of lignosulphonic acids such as calcium lignosulfonate, salts of phenyl sulphonic or naphthalene sulphonic acids, condensed naphthalene sulfonic acid; poly condensates of ethylene oxide with fatty alcohols or fatty acids or fatty esters or fatty amines, or substituted phenols (particularly alkyphenols or arylphenols); salt of sulphonsuccinic acid esters, such as sodium sulfosuccinate; taurine derivatives (particularly alkytauarates); phosphoric esters of alcohols or polycondensates of ethylene oxide with phenols; esters of polyols and of fatty acids or sulfuric acid or sulphonic acids or phosphoric acids; glyceryl esters, especially esters with fatty acids such as glyceryl stearate; ethylene glycols; and the like.

The secondary thickener is a compound which increases the viscosity of a gel or a liquid.

The secondary thickener which may be used in the invention may be selected from among those of the following list (which is non limiting): fumed silica; hydroxyethyl cellulose, carboxy-methylcellulose; organically modified attapulgite or montmorillonite clay; hardened castor oil; cetyl and stearyl alcohols or esters; polyethylene glycols; glyceryl hydroxystearate, polyvinylalcohol; salts of sulphosuccinic acid esters such as the dioctyl sodium sulfosuccinate; salts of benzoic acid such as sodium benzoate; alkyl sulphates.

The gels of the invention can be prepared or manufactured by any known method. A convenient way is to mix together the different constituents of the mixture/composition and to stir them, optionally with grinding or milling and/or heating. The constituents of the composition may be added and mixed randomly or added in several various manners which more conveniently achieve the desired gel properties. As is known to one of ordinary skill in the art, such addition and mixing may be dependent upon the physical and chemical nature of the individual constituents, their combination(s), and the desired final gel. In this regard, sometimes it is easier to operate with a slow addition of the constituents of the composition.

The instant invention also includes containerization systems which comprise water soluble or water dispersible bags containing the gel formulations as hereabove defined.

The chemical nature of the enveloping film constituting the bags which may contain the composition/gels of the invention can vary quite widely. Suitable materials are water soluble (or possibly water dispersible) materials which are insoluble in the organic solvents used to dissolve or disperse the agrochemical active ingredient. Specific suitable materials include polyethylene oxide, such as polyethylene glycol; starch and modified starch; alkyl and hydroxyalkylcellulose, such as hydroxymehtylcellulose, hydroxyethylcellulose, hydroxypropylcellulose, carboxyethylcellulose polyvinylethers such as poly methyl vinylether; poly(2,4-dimethyl-6-triazolyethelene); poly(vinylsulfonic acid); polyanhydrides; low molecular weight urea-formaldehyde resins; low molecular weight melamine-formadehyde resins; poly(2-hydroxyethyl methacrylate); polyacrylic acid and its homologs; but preferably the enveloping film comprises or is made from polyvinylalcohol (PVA).

Preferred material for constituting the bags for the gels of the invention are poly ethyleneoxide or methylcellulose, or polyvinylalcohol. When polyvinylalcohol is used, it is advantageously a 40–100%, preferably 80–99% alcoholized or hydrolysed, polyvinyl acetate film.

The water soluble films which are used to make the water soluble bags are known. To make a bag, the film needs to be shaped (possibly partially sealed) and then filled with the gel. Generally, the gels are able to flow, even if it is a slow rate due to the high viscosity. A container which is used to contain the gels cannot be easily emptied due to this high gel viscosity (that a reason why the gels were not used up to now in the agriculture). When filled, the bag has to be finally sealed, generally heat sealed, to be closed.

According to another feature, the bag of the invention is filled to at least 60% of capacity with the agrochemical composition-containing substance, more preferably at least 70% of capacity, still more preferably 80 to 99% of capacity and most preferably 85 to 95% of capacity. The bag is preferably not filled to complete capacity because the unused capacity gives the bag shock resistance, i.e., resistance to breakage when dropped, transported or stored. This unused capacity may or may not contain air or an inert gas. An absence of air or inert gas in the unused capacity further improves shock resistance. However, in deciding how much unused capacity, or absence of air or inert gas, to provide, the advantages of shock resistance must be balanced against the need, if any, for shock resistance and the cost of providing shock resistance. For example, if the bag is stored and/or transported in a shock absorbing container, then it may not be as helpful to provide this unused capacity.

Also, the capacity to which the bag is filled, and whether the unused capacity does or does not contain air or inert gas is affected by whether it is desired to have the bag sink or float. Whether the bag sinks or floats will depend not only on the unused capacity, but also on the density of the bag contents.

Further information may be found in the following copending applications, the disclosures of which are incorporated herein by reference: U.S. Ser. No. 07/713,683, application of Leonard E. Hodakowski, Chi-Yu R. Chen, Samuel T. Gouge and Paul J. Weber for "Gel Formulations for Use in Toxic or Hazardous Product Containerization Systems" filed June 11, 1991; application of David B. Edwards, William J. McCarthy, Leonard E. Hodakowski, Chi-Yu R. Chen, Samuel T. Gouge and Paul J. Weber for "Laminated Bags for Containerization of Toxic or Hazardous Materials" filed June 11, 1991 application of Samuel T. Gouge, Leonard E. Hodakowski, Paul J. Weber and Chi-Yu R. Chen for "gel Formulations for Hazardous Products" filed June 11, 1991 application of Leonard E. Hodakowski, Ricky W. Couch, Samuel T. Gouge and Robert C. Ligon for "Gel Formulations" filed June 11, 1991; U.S. Ser. No. 07/713,684, and application of Samuel T. Gouge and James E. Shue for "Bag In A Bag for Containerization of Toxic or Hazardous Material" filed June 11, 1991.

The following examples are given for illustrative purposes and should not be understood as restricting the invention.

In those examples, tg(phi) is less than 1.5 and the surfactant satisfies to the test requirement hereabove defined.

EXAMPLE 1

A gel was made by stirring, at 50° C., a mixture of:
Active ingredient:
2,4-D phenoxy benzoic acid isooctyl ester: 64.8%
Solvent:
aromatic solvent with flash point of 65° C.: 24.2%
Surfactant:
a mixture of a non ionic/sulfonate
blended emulsifier: 4% and calcium alkylbenzene sulfonate:
Gelling agent:
mixture of dioctylsulfosuccinate salt and sodium benzoate: 6%.

The mixture is stirred and shaked until each component is dissolved or dispersed.

During stirring, a dissolution appears, and thereafter a gelation. Gelation is increased during the cooling at room temperature (20° C.).

The Brookfield viscosity of the gel is 3000 centipoises.

The emulsion stability is good in the above described test.

1100g of this gel are put in a 1 liter bag made of a film of PVA (88% hydrolysed polyvinyl acetate; cold water soluble; thickness: 55 microns). The bag, which is almost full (about 95% v/v) is heat sealed. The density (specific gravity both of the gel and of the bag containing the gel is 1.1 gm/cc.

The bag is then dropped 10 times from 1.2 m upon the ground. No breaking or leakage is observed.

The bag is put in a tank containing water under gentle agitation (that is to say such as that obtained with pump recycling). It is dispersed within a 3 min. interval. There is no clogging in the filter which is a 100 mesh screen.

Another bag, made in the same way as the previous one, is tested for pinhole protection. A needle (diameter: 0.6 mm) is passed through the bag. A small droplet is observed which forms at the locus where the needle passed. However, this droplet was small enough not to drop from the bag and not to flow along the bag.

EXAMPLE 2

The procedure for Example 1 was repeated, except that a mixture containing the following adjuvants is used:

Surfactant:
non ionic/sulfonate blended emulsifier: 5.2%
Gelling agent:
tetramethyl decynediol: 30%

The Brookfield viscosity of the gel is 3000 centipoises.

The emulsion stability is good in the above described test.

1100g of this gel are put in a 1 liter bag made of a film of PVA (88% hydrolysed polyvinyl acetate; cold water soluble; thickness: 55 microns). The bag, which is almost full (about 95% v/v), is heat sealed. The density both of the gel and of the bag containing the gel is 1.1 gm/cc.

The bag is then dropped 10 times from 1.2 m upon the ground. No breaking or leakage is observed.

The bag is put in a tank containing water under gentle agitation (that is to say such as that obtained with pump recycling). It is dispersed within a 3 min. interval. There is no clogging in the filter which is a 100 mesh screen.

EXAMPLE 3

The procedure for Example 1 was repeated, except that a mixture containing the following adjuvants is used:

Surfactant:
non ionic/sulfonate blended emulsifier: 21.5%
and calcium alkylbenzene sulfonate: 3.7%
Gelling agent:
ethoxylated dialkyphenol: 10%.

The Brookfield viscosity of the gel is 3000 centipoises.

The emulsion stability is good in the above described test.

1100 g of this gel are put in a 1 liter bag made of a film of PVA (88% hydrolysed polyvinyl acetate; cold water soluble; thickness: 55 microns). The bag, which is almost full (about 95% v/v), is heat sealed. The density both of the gel and of the bag containing the gel is 1.1 gm/cc.

The bag is then dropped 10 times from 11.2 m upon the ground. No breaking or leakage is observed.

The bag is put in a tank containing water under gentle agitation (that is to say such as that obtained with pump recycling). It is dispersed within a 3 min. interval. There is no clogging in the filter which is a 100 mesh screen.

EXAMPLE 4

A gel was made by stirring at 50° C. a mixture of:
Active ingredient:

bromoxynil acid (octanoate ester): 18.65%
bromoxynil acid (heptanoate ester): 13.85%
methylchloropropionic acid (isooctyl ester): 37.4%
Solvent:
aromatic solvent with a flash point of 38° C.: 11.1%
Surfactant:
non ionic/sulfonate blender emulsifier: 13%
Gelling agent mixture:
hydrogenated caster oil: 3%
ethoxylated vegetable oil: 3%

These materials are mixed together while shearing with an attritor mixer. The product started to gel in a few minutes.

The Brookfield viscosity of the gel is 3150 centipoises.

The emulsion stability is good in the above described test.

The spontaneity is 20.

1100g of this gel are put in a 1 liter bag made of a film of PVA (88% hydrolysed polyvinyl acetate; cold water soluble; thickness: 55 microns). The bag, which is almost full (about 95% v/v), is heat sealed. The density both of the gel and of the bag containing the gel is 1.1 gm/cc.

The bag is then dropped 10 times from 1.2 m upon the ground. No breaking or leakage is observed.

The bag is put in a tank containing water under gentle agitation (that is to say such as that obtained with pump recycling). It is dispersed within a 10 minute interval. There is no clogging in the filter which is a 50 mesh screen.

EXAMPLE 5

The procedure for Example 4 was repeated, except that a mixture containing the following components is used:

Active ingredient:
bromoxynil octanoate:
bromoxynil heptanoate: 14.0%
methyl chloropropionic acetic acid (isooctyl ester): 36.6%.
Surfactant mixture:
non ionic/sulfonate blended emulsifier: 9.0%
Gelling agent:
diatomaceous earth: 17.0% and dioctyl ester of sodium sulfosuccinic acid and sodium
benzoate: 2.0%
Dispersant:
sodium sulfonate of naphthalene formaldehyde condensate 3.0%.

These materials are mixed together while churning with an attritor mixer. The product started to have the appearance of a smooth paste, and is a gel in a few minutes.

The Brookfield viscosity of the gel is 9000 centipoises.

The emulsion stability is good in the above described test.

The spontaneity is 9.

1100g of this gel are put in a 1 liter bag made of a film of PVA (88% hydrolysed polyvinyl acetate; cold water soluble; thickness: 55 microns). The bag, which is almost full (about 95% v/v), is heat sealed. The density both of the gel and of the bag containing the gel is 1.1 gm/cc.

The bag is then dropped 10 times from 1.2 m upon the ground. No breaking or leakage is observed.

The bag is put in a tank containing water under gentle agitation (that is to say such as that obtained with pump recycling). It is dispersed within a 10 minute interval There is no clogging in the filter which is a 50 mesh screen.

EXAMPLE 6

The procedure of Example 5 was repeated, except that a mixture containing the following components is used:
Active ingredient:
bromoxynil octanoate: 31.5%
bromoxynil heptanoate: 31.5%
atrazine: 44.58%
Solvent:
same as in Example 1: 23.25%
Gelling agent:
mixture of dioctyl sodium sulfosuccinic acid and sodium benzoate: 2.0%
Surfactants:
ethoxylated/propoxylated block copolymer with alkyphenol: 3.6%
alkylarysulfonate of an amine: 5%.
Antifreeze agent:
polyethylene glycol: 1%
Antifoam agent:
polyorganosiloxane: 0.5%.

These materials are mixed together and passed through a bead mill. The product gets the appearance of gelatinous mixture; after about 5 hours, it becomes much more viscous.

The Brookfield viscosity of the gel is 9100 centipoises and is 5200 after stirring for 4 minutes.

The emulsion stability is good in the above described test.

The spontaneity is 11.

1100g of this gel are put in a 1 liter bag made of a film of PVA (88% hydrolysed polyvinyl acetate; cold water soluble; thickness: 55 microns). The bag, which is almost full (about 95% v/v), is heat sealed. The density both of the gel and of the bag containing the gel is 1.1 gm/cc.

The bag is then dropped 10 times from 1.2 m upon the ground. No breaking or leakage is observed.

The bag is put in a tank containing water under gentle agitation (that is to say such as that obtained with pump recycling). It is dispersed within a 5 minute interval. There is no clogging in the filter which is a 100 mesh screen.

EXAMPLE 7

The procedure of Example 6 was repeated, except that a mixture containing the following components is used:
Active ingredient:
bromoxynil octanoate: 33.7%
methyl chloropropionic acetic acid (isooctyl ester): 36.2%
Solvent:
aromatic solvent with a flash point of 65° C.: 3.0%
Surfactant:
non-ionic/sulfonate blended emulsifier: 8.5%
and calcium dodecyl benzene sulfonate: 1.0%
Gelling agent:
tetramethyl decyne diol: 17.6%.

These materials are mixed together while shearing with an attritor mixer. The product started to have the appearance of a smooth paste, and is a gel in a few minutes.

The Brookfield viscosity of the gel is 2200 centipoises.

The emulsion stability is good in the above described test.

The spontaneity is 14.

1100g of this gel are put in a 1 liter bag made of a film of PVA (88% hydrolysed polyvinyl acetate; cold water soluble; thickness: 55 microns). The bag, which is almost full (about 95% v/v), is heat sealed. The density both of the gel and of the bag containing the gel is 1.1 gm/cc.

The bag is then dropped 10 times from 1.2 m upon the ground. No breaking or leakage is observed.

The bag is put in a tank containing water under gentle agitation (that is to say such as that obtained with pump recycling). It is dispersed within a 5 minute interval. There is no clogging in the filter which is a 100 mesh screen.

EXAMPLE 8

The procedure of Example 7 was repeated, except that a mixture containing the following components is used:
Active ingredient and solvent are the same as in Example 7, and amount of active ingredient is the same, solvent is the same but the amount is 10.6%.
Surfactant mixture:
polyarylphenol ethoxylated: 6%
and calcium dodecyl benzene sulfonate: 2%
Gelling agent:
mixture of hexane and hexyne diol: 11.5%

These materials are mixed together while shearing with an attritor mixer. The product started to have the appearance of a smooth paste, and is a gel in a few minutes.

The Brookfield viscosity of the gel is 2500 centipoises.

The emulsion stability is good in the above described test.

The spontaneity is 5.

1100g of this gel are put in a 1 liter bag made of a film of PVA (88% hydrolysed polyvinyl acetate; cold water soluble; thickness: 55 microns). The bag, which is almost full (about 95% v/v), is heat sealed. The density both of the gel and of the bag containing the gel is 1.1 gm/cc.

The bag is then dropped 10 times from 1.2 m upon the ground. No breaking or leakage is observed.

The bag is put in a tank containing water under gentle agitation (that is to say such as that obtained with pump recycling). It is dispersed within a 5 minute interval. There is no clogging in the filter which is a 100 mesh screen.

EXAMPLE 9

The procedure of Example 4 was repeated, except that a mixture containing the following components is used:
Active ingredient:
bromoxynil octanoate: 33.5%
bromoxynil heptanoate: 33.5%
Solvent:
aromatic solvent with a flash point of 65° C.: 17.5%
Surfactant:
non ionic/sulfonate blended emulsifier: 4.5%
and calcium dodecyl benzene sulfonate: 1.0%
Gelling agent:

mixture of dioetyl sodium sulfosuccinate and sodium benzoate: 4.25%
Antifoam agent:
tetramethyl decyne diol: 0.5%.

These materials are mixed together at 50° C. while shearing with an attritor mixer. The product started to have the appearance of a smooth paste, and is a gel in a few minutes.

The Brookfield viscosity of the gel is 4850 centipoises.

The emulsion stability is excellent in the above described test.

The spontaneity is 10.

1100g of this gel are put in a 1 liter bag made of a film of PVA (88% hydrolysed polyvinyl acetate; cold water soluble; thickness; 55 microns). The bag, which is almost full (about 95 % v/v), is heat sealed. The density both of the gel and of the bag containing the gel is 1.1 gm/cc.

The bag is then dropped 10 times from 1.2 m upon the ground. No breaking or leakage is observed.

The bag is put in a tank containing water under gentle agitation (that is to say such as that obtained with pump recycling). It is dispersed within a 3 min. interval. There is no clogging in the filter which is a 100 mesh screen.

EXAMPLE 10

A gel was made by stirring at 50° C. a mixture of:
Active ingredient:
bromoxynil acid (as the octanote ester): 30.15%
bromoxynil acid (as the heptanoate ester): 31.15%
Solvent:
aromatic solvent with a flash point of 38° C.: 22.85%
Surfactant:
polyaryl phenolethoxylated: 6.0%
calcium alkylbenzene sulfonate: 2.0%
Gelling agent mixture:
a clay which has been modified by addition of methyl groups: 6.0%
and propylene carbonate: 2.0%.

These materials are mixed together while shearing with an attritor mixer. The product started to gel in a few minutes.

The Brookfield viscosity of the gel is 4200 centipoises.

The emulsion stability is good in the above described test.

The spontaneity is 38.

1100g of this gel are put in a 1 liter bag made of a film of PVA (88% hydrolysed polyvinyl acetate; cold water soluble; thickness; 55 microns). The bag, which is almost full (about 95 % v/v), is heat sealed. The density both of the gel and of the bag containing the gel is 1.1 gm/cc.

The bag is then dropped 10 times from 1.2 m upon the ground. No breaking or leakage is observed.

The bag is put in a tank containing water under gentle agitation (that is to say such as that obtained with pump recycling). It is dispersed within a 10 min. interval. There is no clogging in the filter which is a 50 mesh screen.

We claim:

1. A water dispersible or water soluble organic gel which is a continuous system comprising effective amounts of:
a hazardous material;
a water soluble or water dispersible surfactant, said surfactant being non ionic or anionic or cationic or a mixture of such surfactants, this surfactant satisfying to the following test: the hazardous material (50 g) and the surfactant (15 g) are added to an amount of water, at 50° C., which is sufficient to bring the volume of the mixture to 100 ml; the mixture is agitated so as to give a homogenous emulsion and this is left to stand for 30 minutes at 50° C. in a graduated cylinder; the amount of oily layer which has separated out, and thus formed a distinct liquid phase, must then be less than 20 ml; and
a gelling agent which is either liquid or solid at 23° C. and which is soluble at less than 10% in the liquid mixture of hazardous material and surfactant above 50° C., this gelling agent having, when it is a solid, a particle size less than 100 microns, and having less than 3% by weight of water.

2. The water dispersible or water soluble organic gel of claim 1, wherein said gelling agent has a particle size less than 20 microns and less than 1% by weight of water.

3. A containerization system comprising a water dispersible or water soluble organic gel according to claim 2, this gel being in a water soluble or water dispersible bag.

4. The water dispersible or water soluble organic gel according to claim 1, wherein the hazardous material is an agrochemical.

5. A containerization system comprising a water dispersible or water soluble organic gel according to claim 4, this gel being in a water soluble or water dispersible bag.

6. The water dispersible or water soluble organic gel according to claim 1, wherein the hazardous material is a plant protection agent or a plant growth regulator or a pesticide or a plant nutrient.

7. A containerization system a comprising a water dispersible or water soluble organic gel according to claim 6, this gel being in a water soluble or water dispersible bag.

8. A containerization system comprising a water dispersible or water soluble organic gel according to claim 1, this gel being in a water soluble or water dispersible bag.

9. The containerization system according to claim 5, wherein the bag is filled to at least 60% of capacity.

10. The containerization system according to claim 8, wherein the bag is filled to at least 70% of capacity.

11. The containerization system according to claim 8, wherein the bag is filled to 80 to 99% of capacity.

12. The containerization system according to claim 8, wherein the bag is filled to 85 to 95% of capacity.

13. The water dispersible or water soluble organic gel according to any one of claims 1, 2, 4 or 6 which further comprises an organic solvent.

14. The water dispersible or water soluble organic gel according to any one of claims 1, 2, 4 or 6 which further comprises the following components:
at least one organic solvent wherein the hazardous product is completely soluble at the given concentration;
a dispersant;
a secondary thickener; and
other additives selected from the group of a stabilizer, an antiforming agent, a buffer and an antifreezing agent.

15. The water dispersible or water soluble organic gel according to claim 14 which further comprises the follwoing quantities of components:

5 to 95% of the surfactant;
0.1 to 50% of the gelling agent; and
0 to 80% of the solvent.

16. The water dispersible or water soluble organic gel according to claim 15, comprising:
1 to 25% of the dispersant; and
0.1 to 30% of the secondary thickener.

17. The water dispersible or water soluble organic gel according to claim 16, wherein said gel comprises:
2 to 8% of said dispersant;
1 to 25% of said secondary thickener; and
0.1 to 10% of said other additives.

18. The water dispersible or water soluble organic gel according to claim 15 which comprises the following quantities of components:
25 to 80% of the hazardous material;
2 to 15% of the surfactant;
2 to 10% of the gelling agent; and
3 to 50% of the solvent.

19. The water dispersible or water soluble organic gel according to any one of claims 1, 2, 4 or 6 which has a viscosity of 600 to 30,000 centipoises.

20. The water dispersible to water soluble organic gel according to claim 19 which has a viscosity of 1000 to 12000 centipoises.

21. The water dispersible or water soluble organic gel according to any one of claims 1, 2, 4 or 6 which has a density greater than 1.0 specific gravity.

22. The water dispersible or water soluble organic gel according to claim 21 which has a density greater than 1.05 specific gravity.

23. The water dispersible or water soluble organic gel according to any one of claims 1, 2, 4 or 6 which has a phase difference phi between the controlled shear stress and the resulting shear strain such that tg(phi) is less than or equal to 1.5.

24. The water dispersible or water soluble organic gel according to claim 23 which has a phase difference phi between the controlled shear stress and the resulting shear strain such that tg(phi) is less than or equal to 1.2.

25. The water dispersible or water soluble organic gel according to any one of claims 1, 2, 4 or 6 which has a spontaneity less than 75.

26. The water dispersible or water soluble organic gel according to claim 25 which has a spontaneity less than 25.

27. The water dispersible or water soluble organic gel according to any one of claims 1, 2, 4 or 6 which comprises a surfactant which is able to form above 70° C. a liquid phase with the hazardous product.

28. The water dispersible or water soluble organic gel according to claim 27 which comprises a surfactant which is able to form above 50° C. a liquid phase with the hazardous product.

29. The containerization system according to any one of claims 8, 3, 5 or 7 wherein said water dispersible or water soluble organic gel further comprises an organic solvent.

30. The containerization system according to any one of claims 8, 3, 5 or 7 wherein said water dispersible or water soluble organic gel further comprises the following components:
at least one organic solvent wherein the hazardous product is completely soluble at the given concentration;
a dispersant;
a secondary thickener; and
other additives selected for the group of a stabilizer, an antifoaming agent, a buffer and an antifreezing agent.

31. The containerization system according to claim 30, wherein said water dispersible or water soluble organic gel further comprises the follwoing quantities of components:
5 to 95% of the surfactant;
0.1 to 50% of the gelling agent; and
0 to 80% of the solvent.

32. The containerization system according to claim 31, said water dispersible or water soluble organic gel comprising:
1 to 25% of the dispersant; and
0.1 to 30% of the secondary thickener.

33. The containerization system according to claim 32, wherein said water dispersible or water soluble organic gel comprises:
2 to 8% of said dispersant;
1 to 25% of said secondary thickener; and
0.1 to 10% of said other additives.

34. The containerization system according to claim 31, said water dispersible or water soluble organic gel comprising the following quantities of components;
25 to 80% of the hazardous material;
2 to 15% of the surfactant;
2 to 10% o the gelling agent; and
3 to 50% of the solvent.

35. The containerization system according to any one of claims 8, 3, 5 or 7, wherein said water dispersible or water soluble organic gel has a viscosity of 600 to 30,000 centipose.

36. The containerization system according to claim 35, wherein said water dispersible or water soluble organic gel has a viscosity of 1000 to 12,000 centi-poise.

37. The containerization system according to any one of claims 8, 3, 5 or 7, wherein said water dispersible or water soluble organic gel has a density greater than 1.0 specific gravity.

38. The containerization system according to claim 37, wherein said water dispersible or water soluble organic gel has a density greater than 1.05 specific gravity.

39. The containerization system according to any one of claims 8, 3, 5 or 7, wherein said water dispersible or water soluble organic gel has a phase difference phi between the controlled shear stress and the resulting shear strain such that tg(phi) is less than or equal to 1.5.

40. The containerization system according to claim 39, wherein said water dispersible or water soluble organic gel has a phase difference phi between the controlled shear stress and the resulting shear strain such that tg(phi) is less than or equal to 1.2.

41. The containerization system according to any one of claims 8, 3, 5 or 7, wherein said water dispersible or water soluble organic gel has a spontaneity less than 75.

42. The containerization system according to claim 41, wherein said water dispersible or water soluble organic gel has a spontaneity less than 25.

43. The containerization system according to any one of claims 8, 3, 5 or 7, wherein said water dispersible or water soluble organic gel comprises a surfactant which is able to form above 70° a liquid phase with the hazardous product.

44. The containerization system according to claim 43, wherein said water dispersible or water soluble organic gel comprises a surfactant which is able to form above 50° C. a liquid phase with the hazardous product.

45. The containerization system according to any one of claims 8, 3, 5 or 7, wherein the bag is made of a material selected from polyethylene oxide; starch and modified starch; alkyl and hydroxyalkylcellulose; carboxymethylcellulose; polyvinylethers; poly(2,4-dimethyl-6-triazolylethylene); poly (vinylsulfonic acid); polyanhydrides; low molecular weight urea-formaldehyde resins; low molecular weight melamine-formaldehyde resins; poly(2-hydroxyethyl metharcylate); polyacrylic acid and its homologs.

46. The containerization system according to any one of claims 8, 3, 5 or 7, wherein the bag is made of a material selected from polyethylene glycol; hydroxymethylcellulose; hydroxyethylcellulose; hydroxypropylcellulose; polymethyl vinylether.

47. The containerization system according to can one of claims 8, 3, 5 or 7, wherein the bag is made of polyethylene oxide or methylcellulose, or polyvinyl alcohol.

48. The containerization system according to claim 347, wherein the polyvinyl alcohol is partially or fully alcohol used or hydrolysed to 40–100% polyvinyl acetate film.

49. The containerization system according to claim 47, wherein the polyvinyl alcohol is alcoholysed or hydrolysed to 80 to 99% polyvinyl acetate film.

* * * * *